United States Patent [19]

Woo et al.

[11] Patent Number: 5,356,709
[45] Date of Patent: Oct. 18, 1994

[54] NON-PVC COEXTRUDED MEDICAL GRADE PORT TUBING

[75] Inventors: Lecon Woo, Libertyville, Ill.; Y. Wilson Cheung, Belchertown, Mass.; Jerry D. Bartos, Murietta, Calif.; Michael T. K. Ling, Vernon Hills, Ill.; Indrajit T. Patel, Algonquin, Ill.; Ying-Cheng Lo, Green Oaks, Ill.

[73] Assignee: Baxter International, Inc., Deerfield, Ill.

[21] Appl. No.: 883,009

[22] Filed: May 14, 1992

[51] Int. Cl.⁵ .............................................. D02G 3/00
[52] U.S. Cl. .................................. 428/376; 428/375; 428/398; 428/407; 428/383; 423/70; 423/222; 423/392; 525/28; 525/57; 525/60; 525/92; 156/294
[58] Field of Search ............... 428/476.3, 375, 373, 428/376, 398, 483, 500, 474.4, 357, 361, 372, 383, 401, 407; 423/222, 70, 392; 525/71, 28, 941, 146, 92, 57, 58, 60; 228/126; 156/294, 296, 298

[56] References Cited

U.S. PATENT DOCUMENTS

| | | |
|---|---|---|
| 3,995,084 | 11/1976 | Berger et al. . |
| 4,087,587 | 5/1978 | Shida et al. . |
| 4,087,588 | 5/1978 | Shida et al. . |
| 4,140,162 | 2/1979 | Gajewski et al. ............ 150/1 |
| 4,233,367 | 11/1980 | Ticknor et al. . |
| 4,322,465 | 3/1982 | Webster . |
| 4,327,726 | 5/1982 | Kwong et al. . |
| 4,407,888 | 10/1983 | Crofts . |
| 4,417,753 | 11/1983 | Bacehowski et al. . |
| 4,479,989 | 10/1984 | Mahal . |
| 4,521,437 | 6/1985 | Storms . |
| 4,562,118 | 12/1985 | Maruhashi et al. . |
| 4,627,844 | 12/1986 | Schmitt . |
| 4,643,926 | 2/1987 | Mueller . |
| 4,657,972 | 4/1987 | Giles, Jr. et al. ............ 525/57 |
| 4,707,389 | 11/1987 | Ward . |
| 4,724,028 | 2/1988 | Zabielski et al. . |
| 4,734,327 | 3/1988 | Vicik . |
| 4,735,855 | 4/1988 | Wofford et al. . |
| 4,753,222 | 6/1988 | Morishita . |
| 4,764,404 | 8/1988 | Genske et al. . |
| 4,767,651 | 8/1988 | Starczewski et al. . |
| 4,772,497 | 9/1988 | Maasola . |
| 4,778,697 | 10/1988 | Genske et al. . |
| 4,803,102 | 2/1989 | Raniere et al. . |
| 4,834,755 | 5/1989 | Silvestrini et al. . |
| 4,915,893 | 4/1990 | Gogolewski et al. . |
| 4,923,470 | 5/1990 | Dumican . |
| 4,996,054 | 2/1991 | Pietsch et al. . |
| 5,085,649 | 2/1992 | Flynn . |

Primary Examiner—Patrick J. Ryan
Assistant Examiner—Merrick Dixon
Attorney, Agent, or Firm—Charles R. Mattenson; Thomas S. Borecki; Robert M. Barrett

[57] ABSTRACT

The present invention provides an improved coextruded medical grade port tubing. The medical grade port tubing provides characteristics that are desirable in the medical industry and therefore can be used as a medical port tubing in, for example, renal therapy or blood donor tubes. To this end, the present invention provides a non-PVC coextruded medical grade port tubing including: an outer layer comprising a blend of polypropylene copolymer and styrene-ethylene-butylene-styrene copolymer; a tie layer; and a core layer including a blend of polyamide and ethylene vinyl acetate.

20 Claims, 1 Drawing Sheet

NON-PVC COEXTRUDED MEDICAL GRADE PORT TUBING

BACKGROUND OF THE INVENTION

The present invention relates generally to materials for making medical grade products. More specifically, the present invention relates to medical grade port tubing.

It is known in the medical industry to house products such as fluids that are administered to a patient in plastic containers. Heretofore, some flexible containers have been constructed from polyvinyl chloride.

It is also known to use medical port tubing (ports) to provide access either to a container or from a container. Such medical port tubing has uses in such therapies as renal and blood. It is also known to construct the medical port tubing from polyvinyl chloride.

In order to make polyvinyl chloride sufficiently flexible, so that it can be used to create flexible containers and port tubing, plasticizers have been added thereto. The toxicity of plasticizers has increasingly become a matter of concern both in processing the material into a product, e.g., container or port tubing, and in the end use of the material. In the medical industry, typically, DEHP and/or epoxidized oils are utilized as plasticizers for polyvinyl chloride. Recently, however, DEHP has become a suspect compound in that there is continued testing to determine if DEHP is a health hazard. Additionally, polyvinyl chloride is perceived to be an environmentally unfriendly material.

Examples of therapies wherein flexible containers including port tubing are used include intravenous therapy, continuous ambulatory dialysis (CAPD), and blood therapy. In CAPD, the container includes a dialysis fluid that can be infused into the peritoneym of the patient through the port tubing that is fused to the container.

Typically, for medical uses, there are a variety of characteristics that a medical port tube should have. Among the characteristics the port tube should exhibit is the ability to be bonded to a material from which the container may be constructed. For example, it is known in manufacturing containers with port tubing to radio frequency RF seal such port tubings to a container. It is also desirable that the port tubing can be heat sealable so as to be compatible with equipment used in certain of the medical industries.

Furthermore, such port tubing should be sufficiently flexible as well as translucent. Additionally, the port tubing, if it is coextruded, must not easily delaminate.

Typically, polyvinyl chloride plasticized with DEHP has been used to achieve these needs. However, as previously noted, the use of DEHP has been under some scrutiny and criticism.

SUMMARY OF THE INVENTION

The present invention provides an improved coextruded medical port tubing that does not include PVC and materials for making same. The material of the present invention provides characteristics that are desirable in the medical industry and therefore can be used to make medical port tubing for use in, for example, renal therapy or blood donor tubes. At the same time, the present invention provides a non-PVC material.

To this end, the present invention provides a non-PVC coextruded medical grade port tubing comprising: an outer layer comprising a blend of polypropylene copolymer and styrene-ethylene-butylene-styrene copolymer; a tie layer; and a core layer comprising a blend of polyamide and ethylene-vinyl acetate.

In an embodiment, the polyamide component comprises at least two separate grades of polyamide. The resultant port tubing is RF sealable, or heat sealable, to an olefinic surface. Such a port tubing eliminates the concerns that have been raised with respect to a DEHP plasticized polyvinyl chloride material.

In an embodiment, the tie layer comprises a blend of polyester, polypropylene copolymer, styrene-ethylene-butylene-styrene copolymer, and ethylenevinyl acetate. Preferably, the tie layer is a blend comprising: approximately 30 to about 60% by weight copolyester; approximately 0 to about 20% by weight polypropylene copolymer; approximately 30 to about 60% by weight styrene-ethylene-butylene-styrene copolymer; and approximately 0 to about 30% by weight ethylene vinyl acetate.

In an embodiment, the outer layer of the port tube comprises approximately 40 to about 99% by weight polypropylene copolymer and approximately 1 to about 60% by weight styrene-ethylene-butylene-styrene copolymer.

An advantage of the present invention is that it provides a non-PVC radio frequency active material. The material is RF sealable to olefinic materials such as polyethylene, polypropylene copolymer, and styrene-ethylene-butylene-styrene copolymer.

A further advantage of the present invention is that it provides a steam and radiation (e.g., gamma) sterilizable material.

Moreover, an advantage of the present invention is that the material is flexible (has a low modulus), is optically clear and blush resistant, has excellent inter laminar strength, good compatibility, is clampable, and provides good extrusion processability.

Still further, an advantage of the present invention is that the material does not generate harmful degradants upon incineration.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Figure 1:
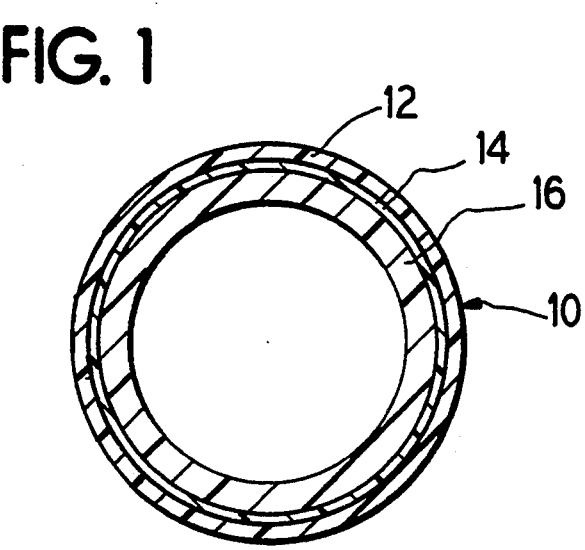
FIG. 1 illustrates a cross-sectional view of a coextruded port tube constructed pursuant to an embodiment of the present invention.

The present invention provides a coextruded medical grade port tubing and material for making the same that achieves many of the characteristics that are desirable, in the medical industry, for such port tubing. For example, the port tubing, in an embodiment, exhibits RF sealability, flexibility, translucence, and ability to resist delamination after severe bending or autoclaving.

At the same time, the present invention provides a port tubing that is constructed from a material that does not include polyvinyl chloride. In this regard, coextruded polyolefin materials are provided that are RF heat sealable to other polyolefins.

To this end, a coextruded medical grade port tubing 10 is provided wherein: the outer layer 12 comprises a blend of polypropylene copolymer and styrene-ethylene-butylene-styrene copolymer; a tie layer 14 preferably comprising a blend of polyester, polypropylene copolymer, styrene-ethylene-butylene-styrene copolymer, and may or may not include ethylene vinyl acetate; and a core layer 16 comprising a blend of polyamide and ethylene vinyl acetate.

The outer layer 12 can comprise approximately 40 to 99% by weight polypropylene copolymer, that includes 2 to 6% by weight polyethylene, and approximately 1 to 60% by weight styrene-ethylene-butylene-styrene copolymer, for example, Kraton. In an embodiment, the outer layer 12 comprises approximately 60% by weight polypropylene copolymer and approximately 40% by weight styrene-ethylene-butylene-styrene copolymer.

Preferably, the core layer 16 comprises ethylene vinyl acetate and polyamide. However, in an embodiment, the polyamide component of the core layer 16 comprises more than one grade of polyamide. In an embodiment, the core layer comprises polyamide Grade No. 1 and polyamide Grade No. 2.

Grade No. 2 polyamide is a softer grade than Grade No. 1 containing less polyamide and therefore is less RF active and less autoclavable. The tertiary blend of two different grades of polyamide and ethylene vinyl acetate in the core layer 16 provides excellent adhesion of the core layer 16 to the tie layer 14.

In an embodiment, the core layer 16 comprises approximately 70% by weight block polyamide and approximately 30% by weight ethylene vinyl acetate. In an embodiment, the core layer 16 comprises approximately 60% by weight block polyamide (Grade No. 1), approximately 20% by weight block polyamide (Grade No. 2), and approximately 20% by weight ethylene vinyl acetate.

The tie layer 14 is used to bridge or bind the two chemically dissimilar materials that define the outer and core layers 12 and 16, respectively. Preferably, the tie layer 14 is a blend of material comprising: approximately 30 to about 60% by weight copolyester, for example, Hytrel available from DuPont; approximately 0 to about 20% by weight polypropylene copolymer (approximately 2–6% by weight polyethylene); approximately 30 to about 60% by weight styrene-ethylene-butylene-styrene copolymer, for example, Kraton; and approximately 0 to about 30% by weight ethylene vinyl acetate.

The tie layer 14 contains both polar and non-polar groups. Thus, it exhibits excellent bonding properties to both the polar core layer 16 material and the non-polar outer layer 12 material. The strong adhesion between the tie layer 14 and the core layer 16 is probably mediated by the interaction of polyester copolymer, ethylene vinyl acetate, and the polyamide. The binding between the tie layer 14 and the outer layer 16 is achieved by the interaction between the styrene-ethylene-butylene-styrene copolymer and the polypropylene copolymer.

The outer layer 12 provides the compatibility required to RF or impulse heat seal the port tubing 10 to an olefinic surface. A high degree of interfacial mixing, indicating excellent bonding performance, is achieved as a direct result of the compatibility between the outer layer 12 and the olefinic surface. Additionally, a strong interlaminar strength is exhibited by the port tubing 10 by the careful selection of materials and the ratio of the respective components.

Preferably, the medical grade port tubing 10 of the present invention has a structure so that it has the following ratio of layer thicknesses: the outer layer 12 comprises approximately 2.5% to about 30% of the total cross-sectional thickness of the port tube 10; the tie layer 14 comprises approximately 2.5% to about 20% of the total cross-sectional thickness of the port tube 10; and the core layer comprises approximately 50 to about 95% of the thickness of the port tube 10.

The port tubing 10 does not include a PVC layer. Accordingly, concerns with respect to PVC and specifically DEHP plasticizer can be avoided by use of the port tubing 10 of the invention.

The port tubing 10 provides a variety of advantages over other known medical grade port tubings including: non-PVC radio frequency active materials; RF heat sealable to olefinic materials such as polyethylene, polypropylene copolymer, and styrene-ethylene-butylene-styrene copolymer; steam or radiation sterilizable; flexibility; optical clarity; excellent interlaminar strengths; good compatibility; does not generate harmful agents upon incineration; good extrusion processability; and it is clampable.

The three layer coextruded tube structure 10, derives its radio frequency response from the core layer 16 which contains highly RF active components such as the polyamide and EVA. These RF active components exhibit dielectric loss exceeding 0.1 at about 27 MHZ.

Figure 2:
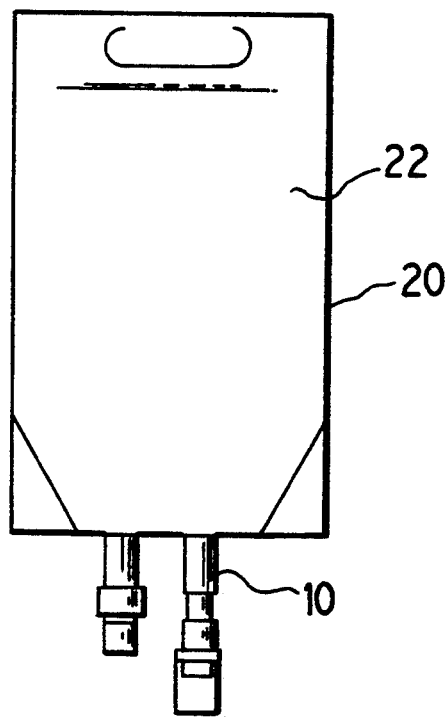
FIG. 2 illustrates a perspective view of a container including the port tubing of the present invention.

The port tubing 10 of FIG. 1 can be used with a medical container 20 illustrated in FIG. 2. The container 20 is constructed from a non-PVC material, for example, a four layer structure as follows: polypropylene copolymer, Kraton/ethylene vinyl acetate/acid modified ethylene vinyl acetate/PCCE.

The port tubing 10 provides fluid communication and access to and from an interior 22 of the container 20. The port tubing 10 of the present invention is believed to be particularly suitable for use in renal applications, especially CAPD. However, the port tubing can be used to construct other medical products.

By way of example, and not limitation, examples of the present invention will now be given.

EXAMPLE NO. 1

Samples of the port tubing of the present invention were constructed using the following two parameters:

| | Sample A |
|---|---|
| Core Layer: | 30% 3315 EVA (DuPont) |
| | 70% 4033 Pebax (Atochem) |
| Tie Layer: | 50 weight % Kraton G-1660 (Shell); |
| | 38 weight % Hytrel 4056 (DuPont); |
| | 10 weight % UE 697000 (Quantum); and |
| | 2 weight % Polypropylene copolymer 23M2 (El Paso); |
| Outer layer: | 60 weight % Polypropylene copolymer Fina 8473 (Fina); and |
| | 40 weight % Styrene-ethylene-butylene-styrene - Kraton G-1652 (Shell). |
| | Sample B |
| Core layer: | 60% Pebax 4033 (Atochem) |
| | 20% Pebax 2533 (Atochem) |
| | 20% EVA 3315 (DuPont) |
| Tie Layer: | 50 weight % Kraton G-1660 (Shell); |
| | 38 weight % Hytrel 4056 (DuPont); |
| | 10 weight % UE 697000 (Quantum); and |
| | 2 weight % Polypropylene copolymer 23M2 (El Paso) |
| Outer layer: | 60 weight % Polypropylene copolymer Fina 8473 (Fina); |

-continued and
40 weight % Styrene-ethylene-butylene-
styrene - Kraton G-1652 (Shell).

These samples were RF sealed to a non-PVC material (polypropylene copolymer, Kraton/ethylene vinyl acetate/acid modified ethylene vinyl acetate/PCCE and tested and provided the following properties:

| Tubing ID | Bulk Pull Force (lb) | Peel Force (lb) |
| --- | --- | --- |
| Sample A | 50 (film break) | 9.2 very good |
|  | 78 (pull out) | 9.1 |
| Sample B | 55 (film delaminate and pull out | 7.7 very good |
|  |  | 7.8 |

These results demonstrate that both samples provide sufficient strength to be used as port tubing in medical applications.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A non-PVC coextruded medical grade port tubing comprising a multi-layer tubing having:
   (a) an outer layer including a blend of (i) polypropylene copolymer and (ii) styrene-ethylene-butylene-styrene copolymer;
   (b) a tie layer disposed adjacent and bonded to the outer layer (a); and
   (c) a core layer disposed adjacent and bonded to said tie layer (b) opposite said outer layer (a) including a blend of (i) polyamide and (ii) ethylene vinyl acetate.

2. The non-PVC medical grade port tubing of claim 1 wherein the tie layer (b) includes a blend of (i) polyester, (ii) polypropylene copolymer, (iii) styrene-ethylene-butylene-styrene copolymer, and (iv) ethylene vinyl acetate.

3. The non-PVC coextruded medical grade port tubing of claim 1 wherein the tie layer (b) is a blend comprising:
   (i) approximately 30 to about 60% by weight copolyester;
   (ii) approximately 0 to about 20% by weight polypropylene copolymer;
   (iii) approximately 30 to about 60% by weight styrene-ethylene-butylene-styrene copolymer; and
   (iv) approximately 0 to about 30% by weight ethylene vinyl acetate.

4. The non-PVC coextruded medical port tubing of claim 1 wherein the outer layer (a) comprises a blend of:
   (i) approximately 40 to about 99% by weight polypropylene copolymer; and
   (ii) approximately 1 to about 60% by weight styrene-ethylene-butylene-styrene copolymer.

5. The non-PVC coextruded medical port tubing of claim 1 wherein the outer layer (a) comprises a blend of (i) approximately 60% by weight polypropylene copolymer and (ii) approximately 40% by weight styrene-ethylene-butylene-styrene.

6. The non-PVC coextruded medical grade port tubing of claim 1 wherein in the core layer (c) the polyamide component (i) includes at least two separate grades of polyamide.

7. The non-PVC coextruded medical grade port tubing of claim 6 wherein the polyamide component (c)(i) includes polyamide Grade No. 1 and polyamide Grade No. 2.

8. The non-PVC coextruded medical grade port tubing of claim 1 wherein the core layer (c) comprises:
   (i) approximately 70% by weight block polyamide; and
   (ii) approximately 30% by weight ethylene vinyl acetate.

9. The non-PVC coextruded medical grade port tubing of claim 1 wherein the core layer (c) comprises:
   (i) a polyamide component including approximately 60% by weight block polyamide (Grade No. 1) and approximately 20% by weight block polyamide (Grade No. 2); and
   (ii) approximately 20% by weight ethylene vinyl acetate.

10. A non-PVC coextruded medical grade port tubing comprising a multi-layer tubing having:
    (a) an outer layer including a blend of (i) polypropylene copolymer and (ii) styrene-ethylene-butylene-styrene copolymer;
    (b) a tie layer disposed adjacent the outer bonded thereto including (i) approximately 30 to about 60% by weight copolyester, (ii) approximately 0 to about 20% by weight polypropylene copolymer, (iii) approximately 30 to about 60% by weight styrene-ethylene-butylene-styrene copolymer, and (iv) approximately 0 to about 30% by weight ethylene vinyl acetate; and
    (c) a core layer disposed adjacent the tie layer and bonded thereto opposite the outer layer including a blend of (i) at least one grade of polyamide and (ii) ethylene vinyl acetate.

11. The non-PVC coextruded medical grade port tubing of claim 10 wherein the outer layer (c) comprises:
    (i) approximately 40 to about 99% by weight polypropylene copolymer; and
    (ii) approximately 1 to about 60% by weight styrene-ethylene-butylene-styrene copolymer.

12. The non-PVC coextruded medical grade port tubing of claim 10 wherein the outer layer (a) comprises (i) approximately 60% by weight polypropylene copolymer and (ii) approximately 40% by weight styrene-ethylene-butylene-styrene.

13. The non-PVC coextruded medical grade port tubing of claim 10 wherein the polyamide component (c)(i) includes polyamide Grade No. 1 and polyamide Grade No. 2.

14. The non-PVC coextruded medical grade port tubing of claim 10 wherein the core layer (c) comprises:
    (i) approximately 70% by weight block polyamide; and
    (ii) approximately 30% by weight ethylene vinyl acetate.

15. The non-PVC coextruded medical grade port tubing of claim 10 wherein the core layer (c) comprises:
    (i) a polyamide component including approximately 60% by weight block polyamide (Grade No. 1) and approximately 20% by weight block polyamide (Grade No. 2); and (ii) approximately 20% by weight ethylene vinyl acetate.

16. A non-PVC medical container for housing medical fluid including a non-PVC coextruded medical grade port tubing that comprises a multi-layer tubing having:
 (a) an outer layer including a blend of (i) polypropylene copolymer and (ii) styrene-ethylene-butylene-styrene copolymer;
 (b) a tie layer disposed adjacent and bonded to the outer layer (a); and
 a core layer disposed adjacent and bonded to the tie layer (b) opposite outer layer (a) including a blend of (i) at least one polyamide and (ii) ethylene vinyl acetate.

17. The non-PVC medical container of claim 16 wherein the tie layer (b) of the medical grade port tubing comprises a blend of (i) polyester, (ii) polypropylene copolymer, (iii) styrene-ethylene-butylene-styrene copolymer, and (iv) ethylene vinyl acetate.

18. The non-PVC medical container of claim 16 wherein the tie layer (b) of the medical grade port tubing is a blend comprising:
 (i) approximately 30 to about 60% by weight copolyester;
 (ii) approximately 0 to about 20% by weight polypropylene copolymer;
 (iii) approximately 30 to about 60% by weight styrene-ethylene-butylene-styrene copolymer; and
 (iv) approximately 0 to about 30% by weight ethylene vinyl acetate.

19. The non-PVC medical container of claim 16 wherein the outer layer (a) of the medical grade port tubing comprises:
 (i) approximately 40 to about 99% by weight polypropylene copolymer; and
 (ii) approximately 1 to about 60% by weight styrene-ethylene-butylene-styrene copolymer.

20. The non-PVC medical container of claim 16 wherein the polyamide component (i) of the core layer (c) of the medical grade port tubing includes at least two separate grades of polyamide.

* * * * *